(12) United States Patent
Pae

(10) Patent No.: US 11,278,100 B2
(45) Date of Patent: Mar. 22, 2022

(54) TRIANGULAR CONTAINER FOR COSMETICS

(71) Applicant: XUYONI Co., Ltd., Seoul (KR)

(72) Inventor: Ju Yeon Pae, Seoul (KR)

(73) Assignee: XUYONI CO., LTD., Seoul (KR)

(*) Notice: Subject to any disclaimer, the term of this patent is extended or adjusted under 35 U.S.C. 154(b) by 0 days.

(21) Appl. No.: 17/057,282

(22) PCT Filed: Nov. 14, 2019

(86) PCT No.: PCT/KR2019/015593
§ 371 (c)(1),
(2) Date: Nov. 20, 2020

(87) PCT Pub. No.: WO2020/145501
PCT Pub. Date: Jul. 16, 2020

(65) Prior Publication Data
US 2021/0212436 A1    Jul. 15, 2021

(30) Foreign Application Priority Data

Jan. 7, 2019  (KR) .................. 20-2019-0000089
Jun. 14, 2019  (KR) .................. 10-2019-0070978

(51) Int. Cl.
*A45D 34/00*   (2006.01)
*B05B 11/00*   (2006.01)
*A45D 40/00*   (2006.01)

(52) U.S. Cl.
CPC ............ *A45D 34/00* (2013.01); *A45D 40/00* (2013.01); *B05B 11/0037* (2013.01);
(Continued)

(58) Field of Classification Search
CPC ............ B05B 11/0037; B05B 11/0038; B05B 11/0054; B05B 11/0089; B05B 11/30;
(Continued)

(56) References Cited

U.S. PATENT DOCUMENTS 2,483,464 A * 10/1949 Johnson ................. B65D 5/001
                                                         229/115
3,702,806 A * 11/1972 Oliva ..................... C12M 23/02
                                                         435/304.1
(Continued)

FOREIGN PATENT DOCUMENTS

KR    20-0438097 Y1    1/2008
KR    20-0446422 Y1    10/2009
(Continued)

OTHER PUBLICATIONS

International Search Report for PCT/KR2019/015593 dated Feb. 27, 2020 from Korean Intellectual Property Office.

*Primary Examiner* — Patrick M. Buechner
(74) *Attorney, Agent, or Firm* — Paratus Law Group, PLLC

(57) ABSTRACT

A cosmetics triangular container for cosmetics which includes: a cover in a triangular column shape including a first opening and having a hollow lower part thereof; an outlet body in a cylindrical shape positioned in the hollow lower part of the cover and moving together with the cover; an inner upper part having an inner space into which the cover and the cylindrical outlet body are inserted together; an inner lower part to which pressure is applied as the cover and the outlet body move up and down; and an outer container in a hollow triangular column shape into which the inner upper part and the inner lower part are to be inserted.

4 Claims, 5 Drawing Sheets

(52) U.S. Cl.
CPC ............... *A45D 2034/007* (2013.01); *A45D 2040/0012* (2013.01); *A45D 2200/054* (2013.01); *B05B 11/0038* (2018.08)

(58) Field of Classification Search
CPC . B05B 11/3001; B05B 11/3042; A45D 34/00; A45D 2034/005; A45D 2034/007; A45D 40/00; A45D 2040/0012; A45D 2200/05; A45D 2200/054; B65D 2583/0445
See application file for complete search history.

(56) References Cited

U.S. PATENT DOCUMENTS

| | | | | |
|---|---|---|---|---|
| D274,499 S | * | 7/1984 | Soos | D9/445 |
| 4,535,902 A | * | 8/1985 | Clark | B29C 49/4278 |
| | | | | 215/382 |
| D321,930 S | * | 11/1991 | Dinand | B65D 77/0493 |
| | | | | D23/360 |
| D496,286 S | * | 9/2004 | Krunas | D9/454 |
| D555,877 S | * | 11/2007 | Reinoso | D9/687 |
| D584,960 S | * | 1/2009 | Sherwood | D9/686 |
| D728,881 S | * | 5/2015 | Gameiro | D32/45 |
| D764,309 S | * | 8/2016 | Yakos | B29C 49/4278 |
| | | | | D9/682 |
| D805,911 S | * | 12/2017 | Borer | C12M 23/02 |
| | | | | D9/561 |
| D895,432 S | * | 9/2020 | Yoshioka | D9/682 |
| D908,965 S | * | 1/2021 | Pae | D28/76 |
| 2008/0023491 A1 | * | 1/2008 | Rousselet | B65D 77/0493 |
| | | | | 222/256 |
| 2011/0024452 A1 | * | 2/2011 | Moretti | B05B 11/00412 |
| | | | | 222/105 |
| 2018/0228336 A1 | * | 8/2018 | Tornaben | A47L 11/4044 |

FOREIGN PATENT DOCUMENTS

| | | |
|---|---|---|
| KR | 10-1218741 B1 | 1/2013 |
| KR | 10-1290354 B1 | 7/2013 |
| KR | 10-2015-0141211 A | 12/2015 |
| KR | 20-0479193 Y1 | 12/2015 |
| KR | 20-0483952 Y1 | 7/2017 |
| KR | 20-2018-0001932 U | 6/2018 |
| KR | 20-0489063 Y1 | 4/2019 |

\* cited by examiner

TRIANGULAR CONTAINER FOR COSMETICS

CROSS-REFERENCE TO PRIOR APPLICATIONS

This application is a National Stage Patent Application of PCT International Patent Application No. PCT/KR2019/015593 (filed on Nov. 14, 2019) under 35 U.S.C. § 371, which claims priority to Korean Patent Application Nos. 20-2019-0000089 (filed on Jan. 7, 2019) and 10-2019-0070978 (filed on Jun. 14, 2019), which are all hereby incorporated by reference in their entirety.

BACKGROUND

The present disclosure relates to a container for cosmetics and, more particularly, to a triangular container for storing cosmetics.

The present disclosure relates to a cosmetic container in a triangular column shape and, more particularly, to a cosmetic container that includes an outer container and an inner part disposed inside the outer container, wherein the inner part includes an upper part 30 and a lower part 50.

In general, there are many types of cosmetic containers, and in the case of liquefied cosmetics or gel-like cosmetics having a low viscosity of 0.01 to 6 poise, such as shampoo, conditioner, lotion, and cleansing cream, a pump-type cosmetic container is used so as to easily eject and use contents stored therein.

Such a coefficient of viscosity is a material-specific constant that indicates a magnitude of fluid viscosity, and is also called a rate of viscosity or the viscosity. The coefficient of viscosity is an important value indicating a degree of viscosity of a fluid, and is generally expressed in units of kg/m·s or Pa·s As a triangular column shape is applied to a cosmetic container, the present disclosure is described not only to enable a user to conveniently use and easily manipulate the cosmetic container but also to provide an aesthetic impression for the user.

In this regard, patents related to a cosmetic container are disclosed in Korean Utility Model Registration No. 20-0479193-0000 (Dec. 24, 2015), Korean Utility Model Application Publication No. 20-2018-0001932 (Jun. 27, 2018), and Korean Patent Application Publication No. 10-2015-0141211 (Dec. 18, 2015), etc., but the patents do not use the triangular column shape as in the present disclosure, and have differences in terms of a pumping method and an outlet structure.

SUMMARY

The present disclosure is described to produce a triangular container provided with an outer container 40, and provided with an inner upper part 30 and an inner lower part 50 installed in the outer container 40.

The present disclosure is described to produce a cosmetic container having a structure in which contents are discharged by a discharge bar 21 protruding through a first opening 11 of a cover while the cover 10 moves up and down in the inner upper part 30.

In addition, in the present disclosure, the outer container 40 is in a triangular column shape and provided with a shape in which there is a curved surface at a part where triangular surfaces of the triangular column meet with each other.

Accordingly, the present disclosure is described to provide better grip feeling in hands when a user holds the container and to increase visual satisfaction of the user.

In addition, the present disclosure is described to have a structure in which a first groove 41a is provided at an upper part of a first curved surface 41 of the outer container, the discharge bar 21 protruding through a second opening 34 of the inner upper part 30 moves up and down along the first groove 41a, and cosmetics stored in the inner lower part 50 are discharged.

In addition, the present disclosure is described to have a structure in which the discharge bar 21 moves until contacting the bottom part 41c, which is an end of the first groove 41a, and then turns back.

In addition, the present disclosure is described to form a concave part 46a on an upper part of a third side surface 46 to facilitate disassembly and assembly of the inner upper part 30.

The present disclosure relates to a triangular container for cosmetics, the triangular container including: a cover 10 in a triangular column shape including a first opening 11 and having a hollow lower part thereof; an outlet body 20 in a cylindrical shape positioned in the hollow lower part of the cover 10 and moving together with the cover 10; an inner upper part 30 having an inner space into which the cover 10 and the cylindrical outlet body 20 are inserted together; an inner lower part 50 to which pressure is applied as the cover 10 and the outlet body 20 move up and down; and an outer container 40 in a hollow triangular column shape into which the inner upper part 30 and the inner lower part 50 are to be inserted.

The cylindrical outlet body 20 may include: a discharge bar 21 protruding to outside through the first opening 11; and a central member 24 connected to the discharge bar 21 and installed inside the outlet body 20, the inner upper part 30 may include: a rim 31 in a triangular shape formed along an upper edge thereof; a second opening 34 formed at a lower part of a corner of the triangular rim 31; and a cylindrical member 33 with a hollow inside disposed therein, the triangular rim 31 may stop at the upper part of the outer container 40, and the discharge bar 21 may be disposed by passing through the second opening 34 of the inner upper part 30 after passing through the first opening 11 of the cover 10.

In addition, the inner lower part 50 may include: a vertical movement member 51 passing through the cylindrical member 33 and into which the central member 24 is fitted; and a spring 56 installed around the vertical movement member 51, wherein the vertical movement member 51, the central member 24, and the discharge bar 21 may be sequentially connected to each other so that the cosmetics in the inner lower part 50 may be discharged by sequentially moving through the vertical movement member 51, the central member 24, and the discharge bar 21.

In addition, when the cover 10 is pressed, the vertical movement member 51, the central member 24, and the discharge bar 21 may move downward together and the spring 56 may be compressed, whereas when external force is removed from the cover 10, the vertical movement member 51, the central member 24, and the discharge bar 21 may also move upward together by force of the spring 56, and the outer container 40 may include: a first side surface 42, a second side surface 44, and a third side surface 46 forming the triangular column shape thereof.

In addition, the outer container 40 may include: a first curved surface 41 convexly formed between the first side surface 42 and the second side surface 44 throughout a longitudinal direction, wherein a first groove 41a may be provided on the first curved surface 41, the discharge bar 21 may move up and down in the second opening 34 and the first groove 41a when the cover 10 is pressed, and the cosmetics inside the inner lower part 50 may be discharged to the outside through the discharge bar 21.

In addition, the triangular container may further include: a second curved surface 43 convexly formed throughout a longitudinal direction between the first side surface 42 and the third side surface 46; and a third curved surface 45 convexly formed throughout a longitudinal direction between the second side surface 44 and the third side surface 46, wherein the second opening 34 of the inner upper part 30 and the first groove 41a may be disposed side by side when the inner upper part 30 is inserted into the outer container 40 and fixed thereto, heights of a bottom part 34a of the second opening 34 and a bottom part of the first groove 41a may be the same, and the discharge bar 21 may be able to move to the bottom part 34a of the second opening 34 and a bottom part 41c of the first groove 41a when the discharge bar 21 descends along the second opening 34 of the inner upper part 30 and the first groove 41a.

The present disclosure is described to produce a container in a triangular column shape, the container being provided with an outer container 40 and provided with an inner upper part 30 and an inner lower part 50 installed in the outer container 40, thereby offering a user with an aesthetic impression and convenience in use.

As a cover 10 moves up and down in the inner upper part 30, contents are allowed to be discharged through a discharge bar 21, thereby providing convenience in use.

In addition, in the present disclosure, the outer container 40 has an outward appearance in a triangular column shape, and has a curved surface shape at a part where surfaces of the triangular column shape meet with each other, thereby providing a user better grip feeling in hands when holding the container, and also increasing visual satisfaction of the user.

In addition, the present disclosure is described to have a structure in which a first groove 41a is provided at an upper part of the first curved surface 41 of the outer container, the discharge bar 21 moves up and down along the first groove 41a, and cosmetics stored in the inner lower part 50 is discharged.

In addition, the present disclosure is described to have a structure in which the discharge bar 21 moves until contacting a bottom part 41c, which is an end of the first groove 41a, and then turns back, thereby providing convenience in use for the user.

In addition, in the present disclosure, a concave part 46a is formed in a third side surface 46, thereby facilitating disassembly and assembly of the inner upper part 30.

In addition, in the present disclosure, the upper part of the inner upper part 30 is provided with a rim 31 protruding in a hollow triangular shape, so that the cover 10 is inserted inside the rim, thereby facilitating the assembly and disassembly.

DETAILED DESCRIPTION

Hereinafter, the present disclosure will be described in more detail with reference to the drawings.

The accompanying drawings show exemplary forms of the present disclosure, which are provided only to describe the present disclosure in more detail, and the technical scope of the present disclosure is not limited thereto.

Figure 1:
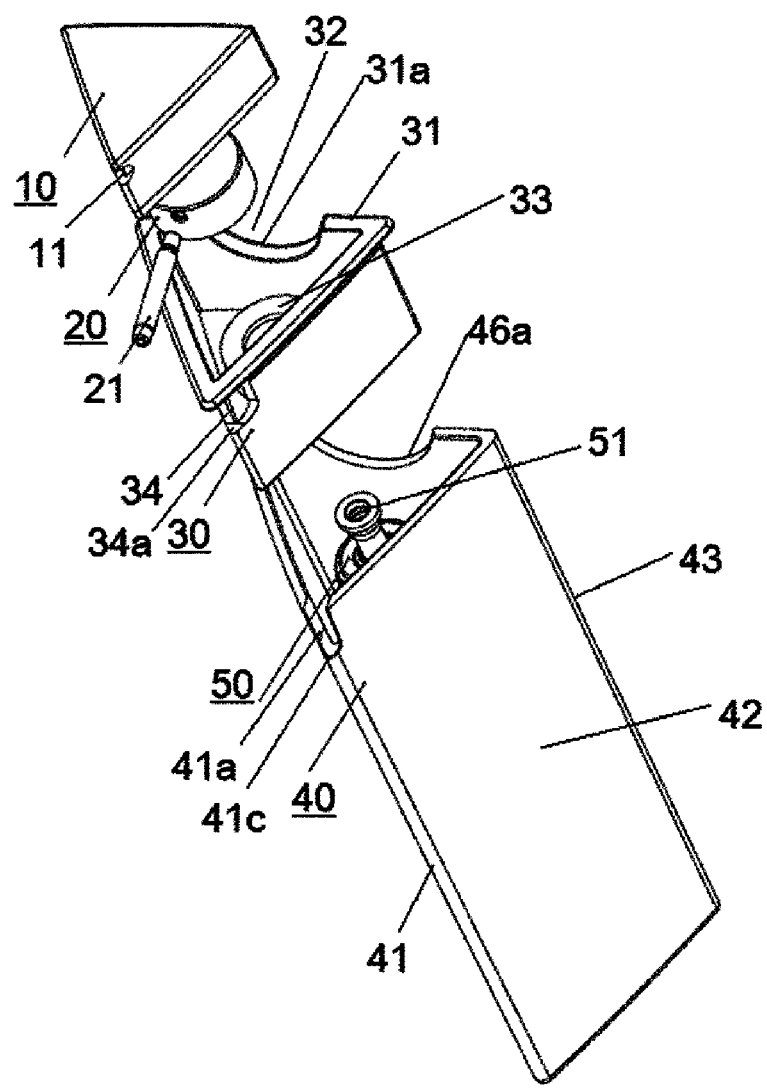
FIG. 1 is an exploded perspective view showing a container of the present disclosure.
Figure 2:
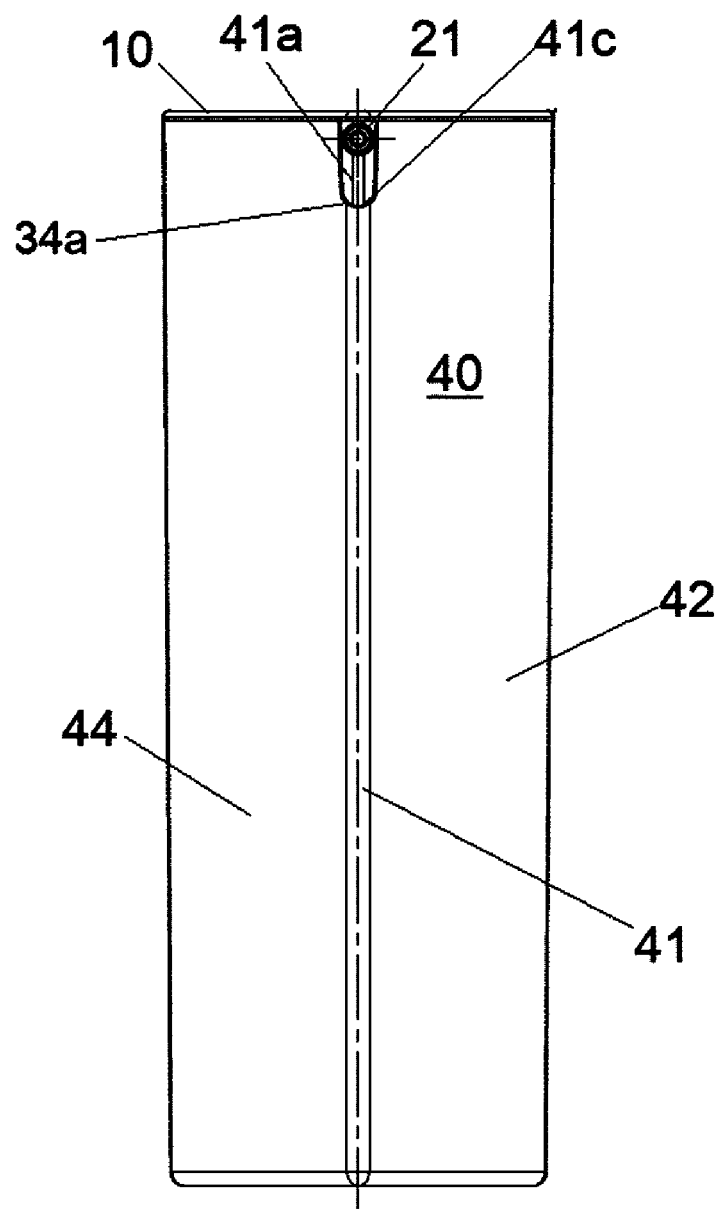
FIG. 2 is a front view showing the container of the present disclosure.
Figure 3:
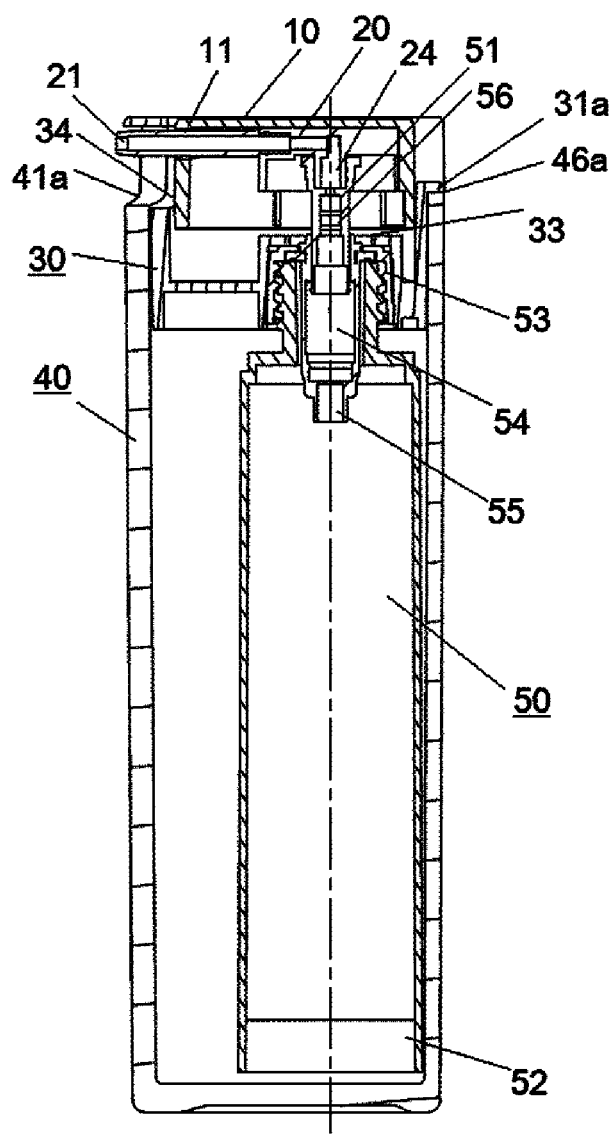
FIG. 3 is an internal perspective view of the present disclosure.
Figure 4:
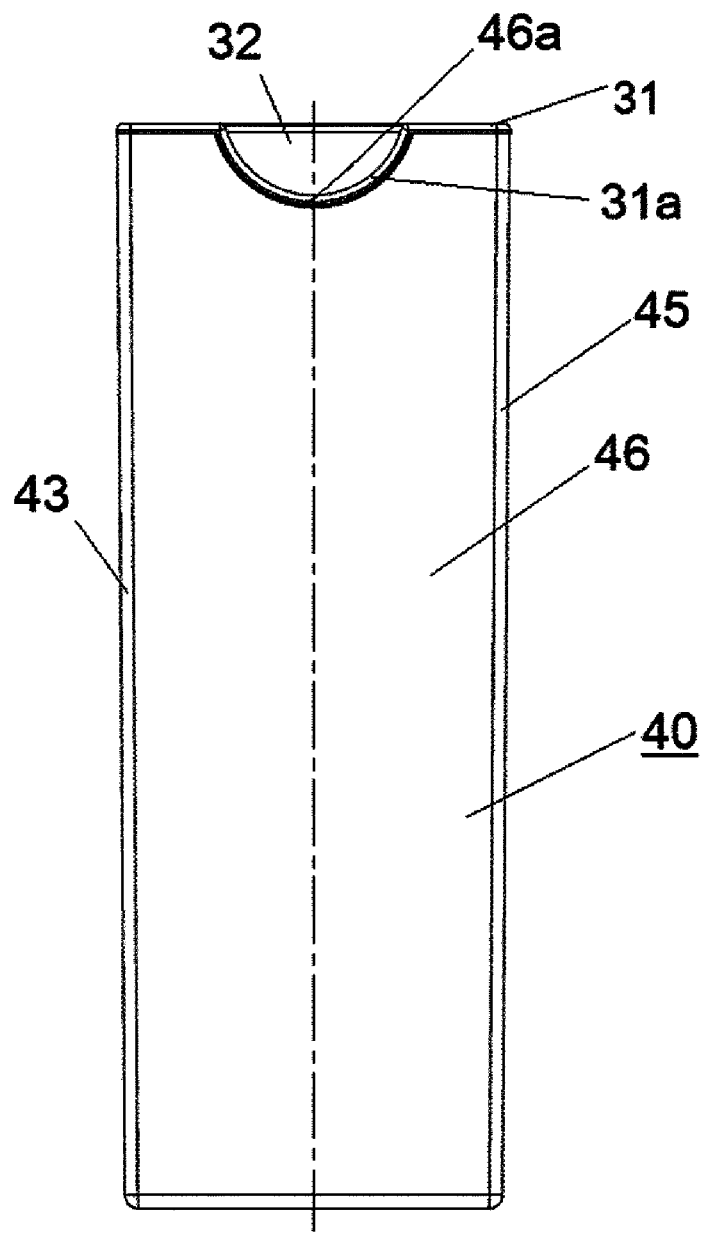
FIG. 4 is a rear view showing the container of the present disclosure.
Figure 5:
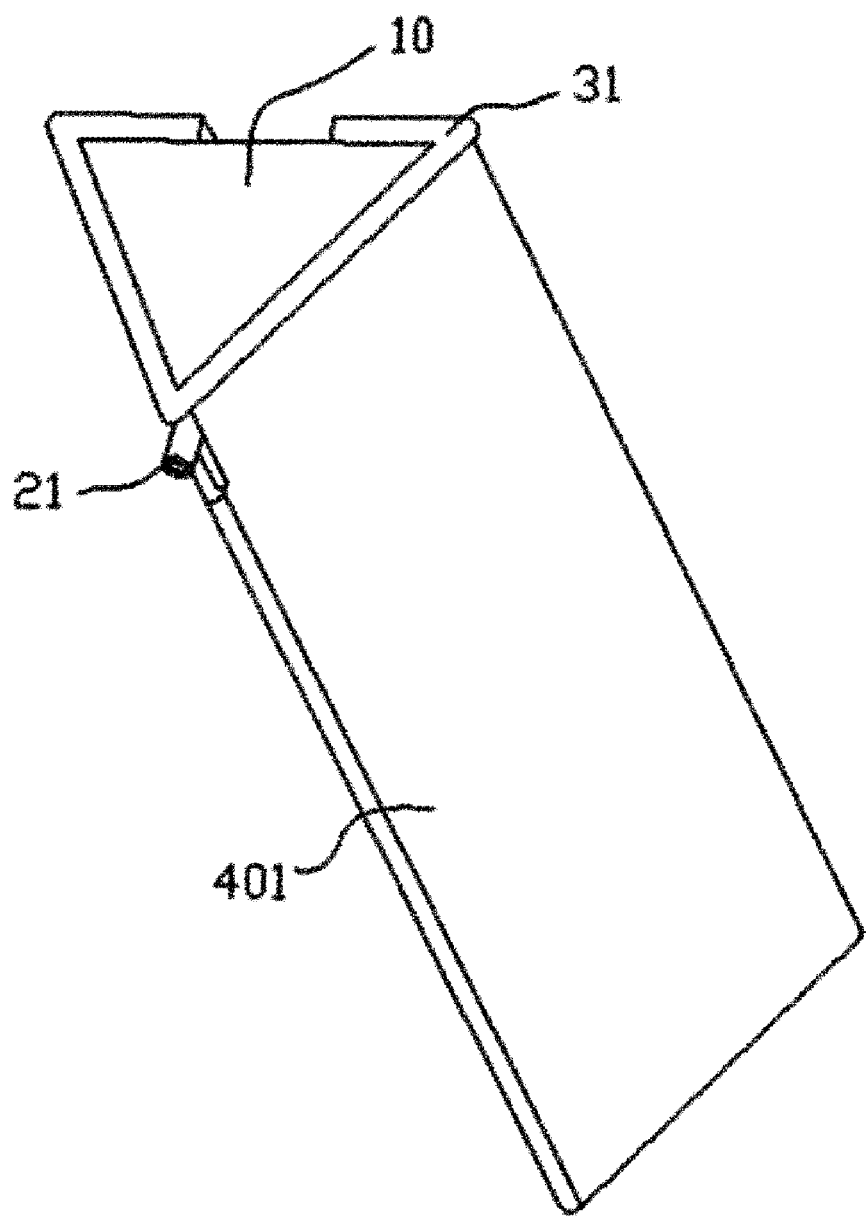
FIG. 5 is a perspective view showing the container of the present disclosure.

FIG. 1 is a perspective view of the present disclosure, including a cover 10, an outlet body 20, an inner upper part 30, an inner lower part 50, and an outer container 40.

A discharge bar 21 of the outlet body 20 has a structure in which the discharge bar 21 passes through a first opening 11 of the cover 10, and the outlet body 20 and the cover 10 are placed inside the inner upper part 30.

In addition, the discharge bar 21 protrudes to outside through a second opening 34 of the inner upper part 30.

That is, the discharge bar 21 protrudes to the outside through the first opening 11 of the cover 10 and the second opening 34 of the inner upper part 30.

When the cover 10 is pressed, the outlet body 20 descends together, pressure is applied to the inner lower part 50, and cosmetics existing inside the inner lower part 50 are discharged to the outside through the discharge bar 21.

In addition, the inner upper part and the inner lower part are fitted inside the outer container 40.

The outer container 40 includes: a first side surface 42, a second side surface 44, and a third side surface 46 forming a triangular column shape thereof; a first curved surface 41 convexly formed throughout the longitudinal direction between the first side surface 42 and the second side surface 44; a second curved surface 43 convexly formed throughout the longitudinal direction between the first side surface 42 and the third side surface 46; and a third curved surface 45 convexly formed throughout the longitudinal direction between the second side surface 44 and the third side surface 46.

A first groove 41a is formed at an upper part of the first curved surface 41 in a longitudinal direction (i.e., in a longitudinal direction of the container). When the inner upper part 30 is inserted into the outer container 40 and fixed thereto, the second opening 34 of the inner upper part 30 and the first groove 41a are disposed side by side, and also the heights of the bottom part 34a of the second opening 34 and the bottom part of the first groove 41a are the same.

The discharge bar 21 moving together with the cover 10 moves up and down along the second opening 34 of the inner upper part 30 and the first groove 41a, and moves to the bottom part 34a of the second opening 34 and the bottom part 41c of the first groove 41a.

In addition, in the present disclosure, the upper part of the inner upper part 30 is provided with a rim 31 in a hollow triangular shape, and the second opening 34 is formed at a lower part of one corner of the rim 31.

An inner space into which the cover 10 and the outlet body 20 are inserted is formed inside the rim.

In addition, when the inner upper part 30 is inserted into the outer container 40, the rim 31 is stopped on the upper part of the outer container 40.

A concave part 46a is formed on an upper part of the third side surface 46, and a concave part 31a corresponding to the concave part 46a is formed in a part of the rim 31, so that the concave part 31a of the rim 31 is matched with the concave part 46a of the third side surface 46 when the inner upper part 30 is inserted into the outer container 40.

A central member 24 in a cylindrical shape is provided inside the outlet body 20, and the central member 24 may be inserted inside a vertical movement member 51 of the inner lower part 50.

The discharge bar 21, the central member 24, and the vertical movement member 51 are sequentially connected to each other, and the discharge bar 21, the central member 24, and the vertical movement member 51 each have a through hole therein through which cosmetics may pass.

In addition, the vertical movement member 51 protrudes upward by passing through a hollow cylindrical member 33 of the inner upper part 30, and a spring 56 is installed on an outer circumference of the vertical movement member 51, so that the vertical movement member 51 moves upward by force of the spring 56 when no external force is applied (i.e., when force is not given to the vertical movement member 51 through the cover).

The spring 56 is installed between the cylindrical member 33 and the rim protruding from an upper end of the vertical movement member 51, and applies the force that moves the vertical movement member 51 upward with respect to the cylindrical member 33.

In addition, when a user applies force to the cover 10 to move downward, the vertical movement member 51 moves downward through a passage 54 and applies pressure to the inner lower part 50.

As the vertical movement member 51 moves up and down, the pressure is applied to the inner lower part 50, and as a bottom member 52 moves upward, the cosmetics contained in the inner lower part 50 is pushed upward.

All the discharge bar 21, the central member 24, and the vertical movement member 51 respectively have hollow shapes with holes formed therein, whereby the cosmetics stored in the container are discharged to the outside therethrough.

Although exemplary aspects of the present disclosure have been described for illustrative purposes, those skilled in the art will appreciate that various modifications, additions, and substitutions are possible without departing from essential characteristics of the present disclosure. Therefore, the exemplary embodiments disclosed in the present disclosure are not intended to limit the technical idea of the present disclosure but to describe the present disclosure, and the technical idea of the present disclosure is not limited by these exemplary embodiments. The scope of protection of the present disclosure should be interpreted by the following claims, and all technical ideas within the scope equivalent thereto should be construed as being included in the scope of the present disclosure.

The invention claimed is:

1. A triangular container for cosmetics, the triangular container comprising:
    a cover in a triangular column shape comprising a first opening and having a hollow lower part thereof;
    an outlet body in a cylindrical shape positioned in the hollow lower part of the cover and moving together with the cover;
    an inner upper part having an inner space into which the cover and the cylindrical outlet body are inserted together;
    an inner lower part to which pressure is applied as the cover and the outlet body move down, wherein the inner lower part contains the cosmetics therein; and
    an outer container in a hollow triangular column shape into which the inner upper part and the inner lower part are to be inserted, wherein the outer container has an upper part,
    wherein the cylindrical outlet body comprises:
    a discharge bar protruding to outside through the first opening; and
    a central member connected to the discharge bar and installed inside the outlet body,
    the inner upper part comprises:
    a rim in a triangular shape formed along an upper edge thereof;
    a second opening formed at a lower part of a corner of the triangular rim; and
    a cylindrical member with a hollow shape disposed therein,
    wherein the triangular rim stops at the upper part of the outer container, and
    the discharge bar is disposed by passing through the second opening of the inner upper part after passing through the first opening of the cover.

2. The triangular container of claim 1, wherein the inner lower part comprises:
    a vertical movement member passing through the cylindrical member and into which the central member is fitted; and
    a spring installed around the vertical movement member,
    wherein the vertical movement member, the central member, and the discharge bar are sequentially connected to each other so that the cosmetics in the inner lower part are discharged by sequentially moving through the vertical movement member, the central member, and the discharge bar.

3. The triangular container of claim 2, wherein, when the cover is pressed, the vertical movement member, the central member, and the discharge bar move downward together and the spring is compressed, whereas when external force is removed from the cover, the vertical movement member, the central member, and the discharge bar also move upward together by force of the spring,
    the outer container comprises:
    a first side surface, a second side surface, and a third side surface forming the triangular column shape thereof; and
    a first curved surface convexly formed between the first side surface and the second side surface throughout a longitudinal direction,
    wherein a first groove is provided at an upper part of the first curved surface,
    the discharge bar moves up and down in the second opening and the first groove when the cover is pressed, and
    the cosmetics inside the inner lower part are discharged to the outside through the discharge bar.

4. The triangular container of claim 3, further comprising:
    a second curved surface convexly formed throughout a longitudinal direction between the first side surface and the third side surface; and
    a third curved surface convexly formed throughout a longitudinal direction between the second side surface and the third side surface,
    wherein the second opening of the inner upper part and the first groove are disposed side by side when the inner upper part is inserted into the outer container and fixed thereto,
    heights of a bottom part of the second opening and a bottom part of the first groove are the same, and the discharge bar is able to move to the bottom part of the second opening and a bottom part of the first groove when the discharge bar descends along the second opening of the inner upper part and the first groove.

\* \* \* \* \*